United States Patent [19]

Hermecz et al.

[11] 4,456,752

[45] Jun. 26, 1984

[54] PROCESS FOR THE PREPARATION OF 9-HYDRAZONO-6,7,8,9-TETRAHYDRO-4H-PYRO[1,2-A]PYRIMIDINE-4-ONE COMPOUNDS, THE SALTS AND HYDRATES THEREOF

[75] Inventors: István Hermecz; Tibor Breining; Lelle Vasvári neé Debreczy; Ágnes Horváth, all of Budapest; József Kökösi, Budaörs, all of Hungary

[73] Assignee: Chinoin Gyogyszer es Vegyeszeti Termekek Gyara R.T., Budapest, Hungary

[21] Appl. No.: 327,689

[22] Filed: Dec. 4, 1981

Related U.S. Application Data

[63] Continuation of Ser. No. 148,240, May 9, 1980, abandoned.

[30] Foreign Application Priority Data

May 11, 1979 [HU] Hungary .............................. CI 1934

[51] Int. Cl.³ ......................................... C07D 471/04
[52] U.S. Cl. .................................... 544/116; 544/282
[58] Field of Search ............... 544/282, 116; 542/419, 542/432, 458; 564/250, 251

[56] References Cited

U.S. PATENT DOCUMENTS 3,141,043 7/1964 McBee ................................ 564/250
4,234,586 11/1980 Hermecz et al. ................... 424/251

FOREIGN PATENT DOCUMENTS 0883219 9/1980 Belgium .
3017560 11/1980 Fed. Rep. of Germany .
3017564 11/1980 Fed. Rep. of Germany .

OTHER PUBLICATIONS

Smith, "The Chemistry of Open-Chain Organic Nitrogen Compounds", vol. II, Derivatives of Oxidized Nitrogen: Hydrazines to Nitrates, W. A. Benjamin, Inc., New York, p. 172, (1966).

Theilacker et al., *Annalen der Chemie*, 572, pp. 121–144, 1951.

*Primary Examiner*—Mary C. Lee
*Assistant Examiner*—Diana G. Rivers
*Attorney, Agent, or Firm*—Karl F. Ross; Herbert Dubno

[57] ABSTRACT

A process for the preparation of nitrogen bridgehead condensed pyrimidine compounds of the general formula

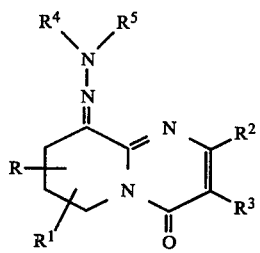

[wherein
R represents hydrogen or lower alkyl;
$R^1$ represents hydrogen, lower alkyl, carboxy or a derivative thereof or styryl;
$R^2$ represents hydrogen or optionally substituted lower alkyl;
$R^3$ represents hydrogen, optionally substituted lower alkyl, aryl, aralkyl, halogen, carboxy or a derivative thereof, the group —$(CH_2)_m$—COOH (in which m is the integer 1, 2 or 3) or a carboxy derivative thereof, formyl, lower alkanoyl or a condensed thereof;
$R^4$ represents hydrogen, optionally substituted alkyl, aryl optionally substituted by one or more substituents, optionally substituted aralkyl, a heterocyclic group optionally substituted by one or more substituents, the group $(CH_2)_m$—Het (in which m is the integer 1, 2 or 3; Het is an optionally substituted heterocyclic group);
$R^5$ represents hydrogen, $C_{1-6}$alkyl, aryl optionally substituted by one or more substituents, formyl, lower alkanoyl, optionally substituted aroyl or heteroaryl; or
$R^4$ and $R^5$ together with the nitrogen therebetween represent an optionally substituted mono- or bicyclic heterocyclic ring optionally containing further heteroatom]

and pharmaceutically acceptable salts, hydrates, stereoisomers, optically active isomers, geometrical isomers and tautomers thereof.

3 Claims, No Drawings

PROCESS FOR THE PREPARATION OF 9-HYDRAZONO-6,7,8,9-TETRAHYDRO-4H-PYRO[1,2-A]PYRIMIDINE-4-ONE COMPOUNDS, THE SALTS AND HYDRATES THEREOF

This is a continuation of application Ser. No. 148,240, filed May 9, 1980 now abandoned.

The present invention relates to a process for the preparation of 9-hydrazono-6,7,8,9-tetrahydro-4H-pyrido[1,2-a]pyrimidine-4-one compounds, the salts and hydrates thereof, certain to new compounds and to pharmaceutical compositions containing them. The compounds possess antiallergic and/or antiasthmatic properties.

It is well known that certain pyrido[1,2-a]pyrimidine derivatives possess analgesic and CNS influencing activity (British Patent Specification Ser. No. 1,209,946). One of the most preferred representatives of these compounds is 3-(ethoxycarbonyl)-1,6-dimethyl-4-oxo-6,7,8,9-tetrahydro-4H-pyrido[1,2-a]pyrimidinium methosulfate (PROBON$^R$, Rimazolium) (Arzneimittel Forschung, 22/1972/815) which is widely used in clinical practice as an analgesic. Pyrido[1,2-a]pyrimidine derivatives are prepared from the corresponding (2-pyridylaminomethylene)-malonic acid dialkyl esters by ring closure. Further substituted pyrido[1,2-a]pyrimidine compounds are disclosed in the British Patent Specification Ser. No. 1,454,312.

According to one feature of the present invention there is provided a new process for the preparation of partially new compounds of the formula

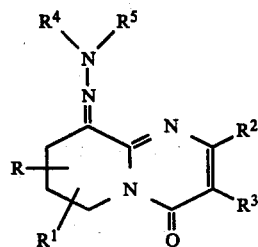

wherein

R is hydrogen or lower alkyl;

$R^1$ is hydrogen, lower alkyl, carboxy or a derivative thereof or styryl;

$R^2$ is hydrogen or substituted or unsubstituted lower alkyl;

$R^3$ is hydrogen, substituted or unsubstituted lower alkyl, aryl, aralkyl, halogen, carboxy or a derivative thereof, the group —$(CH_2)_m$—COOH in which m is an integer 1, 2 or 3) or a carboxy derivative thereof, formyl, lower alkanoyl or a condensed derivative thereof;

$R^4$ is hydrogen substituted or unsubstituted alkyl, aryl which can be substituted by one or more substituents, substituted or unsubstituted aralkyl, a heterocyclic group which can be substituted by one or more substituents, the group —$(CH_2)_m$—Het in which m is the integer 1, 2 or 3 and Het is a substituted or unsubstituted heterocyclic group;

$R^5$ is hydrogen, $C_{1-6}$alkyl, aryl which can be substituted by one or more substituents, formyl, lower alkanoyl, substituted or unsubstituted aroyl or heteroaroyl; or $R^4$ and $R^5$ together with the nitrogen therebetween represent a substituted or unsubstituted mono or bicyclic heterocyclic ring which can containing one or more further heteroatoms.

The term "lower alkyl" used herein for alkyl groups or alkyl-containing groups, such as alkoxy groups, generally stands for $C_{1-6}$, preferably $C_{1-4}$ straight or branched chain aliphatic saturated hydrocarbons, such as methyl, ethyl, n-propyl, isopropyl, n-butyl, secondary butyl, tertiary butyl, n-pentyl, neo-pentyl, n-hexyl etc.

The term "derivative of a carboxy group" refers to conventional carboxylic acid derivatives, such as alkoxycarbonyl e.g. lower alkoxycarbonyl, aryloxycarbonyl, aralkoxycarbonyl or other esters, carbamoyl which can be substituted by one or two alkyl (e.g. lower alkyl), aryl or aralkyl groups; cyano, carboxylic acid hydrazido or hydroxamic acid (—CO—NHOH).

The term "aryl" used as such or in aryl-containing groups such as aryloxy may, for example, stand for substituted or unsubstituted $C_{6-10}$ aromatic groups, such as phenyl or naphthyl or substituted derivatives thereof.

The term "aralkyl" used as such or in aralkyl-containing groups, such as aralkyloxy, may, for example, stand for $C_{1-3}$alkyl substituted by phenyl or naphthyl, such as benzyl, $\beta$-phenyl-ethyl, $\alpha,\beta$-diphenyl-ethyl and $\beta,\beta$-diphenyl-ethyl.

The term "lower alkanoyl" as used herein can stand for groups containing 1 to 4 carbon atoms in the alkyl moiety, preferably alkane carboxylic acid radicals, such as formyl, acetyl, propionyl and butyryl.

The term "a condensed derivative of a lower alkanoyl group" as used throughout the specification can stand for lower alkanoyl groups condensed with a primary or secondary amine, such as dimethyl amine and N-methyl-aniline.

The term "optionally substituted alkyl" as used herein can, stand for alkyl groups which can be substituted with hydroxyl, halogen, carboxy or a derivative thereof, amino, substituted amino, alkoxy or alkanoyloxy, such as trifluoromethyl, hydroxyethyl, aminoethyl, carboxymethyl, $\beta$carboxy-ethyl, etc.

The term "heteroaryl" can stand for heterocyclic carboxylic acid radicals, such as pyperidine-2-, 3- or 4-carboxylic acid, or furan-carboxylic acid.

The term "aroyl" indicated acid radicals of aromatic carboxylic acids, such as substituted or unsubstituted benzoyl groups.

The term "heterocyclic group" stands for mono- or bicyclic rings containing 1 to 4 nitrogens, oxygens and/or sulfurs, as substituted or unsubstituted aromatic or partially or completely saturated rings, such as thienyl, furyl, pyrrolyl, pyridyl, pyrimidinyl, pyrazinyl, pyridazinyl, quinolyl, isoquinolyl, benzofuranyl, benzoxazolyl, oxazolyl, oxadiazolyl, imidazolyl, benzimidazolyl, indolyl, benzothiazolyl, benzisothiazolyl, tetrazolyl, thiadiazolyl, triazinyl, piperidinyl, morpholinyl, pyrrolidinyl and piperazinyl, N-methyl-piperazinyl.

The group "—$NR^4R^5$" can stand for a five or six membered which can condensed group, optionally contain further nitrogen, oxygen or sulfur atoms, such as pyrrolyl, pyrrolidinyl, pyrrolinyl, piperidinyl, morpholinyl, thiomorpholinyl, 1,2,3,4-tetrahydro-quinolyl or 1,2,3,4-tetrahydro-isoquinolyl.

The aryl groups, the aryl group of the aralkyl groups and the heterocyclic groups can be substituted by one or more suitable groups or atoms, such as halogen, e.g. chlorine, bromine, iodine or fluorine; lower alkyl, e.g. methyl or ethyl; lower alkoxy, e.g. methoxy, ethoxy; lower alkylenedioxy, e.g. methylenedioxy, ethylenedioxy or propylenedioxy; mono-, di- or trihalogenalkyl, e.g. trifluoromethyl, amino, alkanoylamino, substituted amino, carboxy or derivatives thereof, sulfonic acid or salt, ester thereof, hydroxy, alkanoyloxy, aroyloxy, heteroaroyloxy, nitro, mercapto, or lower alkylthio.

Preferred compounds prepared according to the present invention include compounds of the formula I, wherein R is hydrogen;

$R^1$ is hydrogen, lower alkyl, preferably methyl, styryl or lower alkoxycarbonyl, preferably methoxycarbonyl or ethoxycarbonyl;

$R^2$ is hydrogen, or lower alkyl, preferably methyl;

$R^3$ is carboxy, lower alkoxycarbonyl, preferably methoxycarbonyl or ethoxycarbonyl, carbamoyl, cyano, formyl, lower alkyl, preferably methyl, or phenyl;

$R^4$ is hydrogen, lower alkyl, preferably methyl, hydroxyethyl, carboxyalkyl, optionally substituted phenyl or naphthyl, trifluoromethyl, benzyl, 2-, 3- or 4-pyridyl, benzothiazol-2-yl, methoxycarbonyl or ethoxycarbonyl;

$R^5$ is hydrogen, lower alkanoyl, preferably acetyl, benzoyl or nicotinoyl; or the group $-NR^4R^5$ stands for piperidinyl, pyrrolidinyl or morpholinyl.

$R^4$ preferably represents phenyl, which can have one, two or three substituents in o-, m- and/or p-position, selected from hydroxy, halogen, lower alkyl, sulfonic acid, carboxy or derivatives thereof, alkoxy, alkylenedioxy, preferably methylenedioxy, amino, alkoxy, substituted amino, nitro and trifluoromethyl.

An especially preferred class of compounds of the formula I includes those compounds, in which R represents hydrogen, $R^1$ is 6-methyl, $R^2$ is hydrogen, $R^3$ stands for carboxy, $R^4$ is stands substituted or unsubstituted $R^5$ is hydrogen and pharmaceutically acceptable salts thereof.

The compounds of the formula I form salts with pharmaceutically acceptable organic and inorganic acids. Hydrochlorides, hydrobromides, hydroiodides, sulfates, nitrates, phosphates, maleates, malates, succinates, acetates, tartarates, lactates, fumarates, and citrates may, for example, be formed.

Compounds of the formula I containing carboxy or sulfonic acid groups form salts with pharmaceutically acceptable bases, such as alkali metal salts, e.g. sodium or potassium salts; alkali earth metal salts, e.g. calcium or magnesium salts, ammonium salts; and with organic amines, such as triethylamine salts, and ethanolamine salts.

The invention provides optical and geometrical isomers and tautomers of the compounds of the formula I as well. The structure of geometric isomers is shown by the formulae

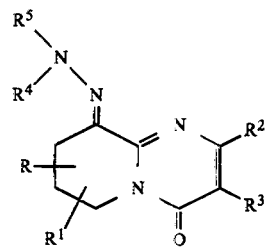

and

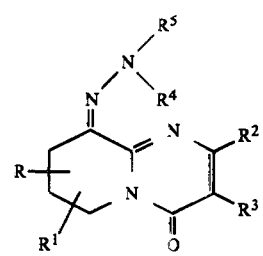

The structure of the tautomers is shown by the relationship A:

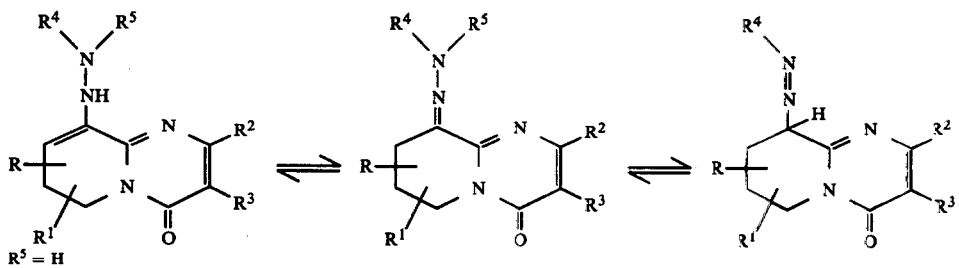

According to the invention the compounds of the formula I, pharmaceutically acceptable salts thereof, hydrates, optically active, geometric and stereoisomers and tautomers thereof are prepared by reacting a compound of the formula

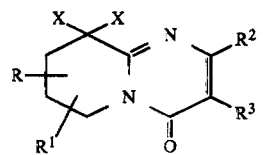

wherein R, $R^1$, $R^2$ and $R^3$ are as hereinbefore defined and X represents halogen, with a compound of the formula

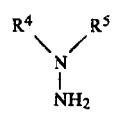

wherein $R^4$ and $R^5$ are as defined hereinabove.

In the compounds of the formula II used starting materials X preferably stands for chlorine, bromine or iodine. The compound of the formula III is preferably used in an amount of 1 to 3 molar equivalent. The reaction of compounds of the general formulae II and III is preferably conducted in the presence of an acid binding agent. As acid binding agents preferably alkali metal carbonates, such as sodium or potassium carbonate, alkali metal hydrogen carbonates, such as sodium or potassium hydrogen carbonate, alkali metal salts of weak acids, such as sodium acetate or an excess or the starting material of the formula III are employed. The reaction can optionally be carried out in an inert solvent. As reaction medium preferably aromatic hydrocarbons, such as benzene, toluene, xylene; esters, such as ethyl acetate; alcohols, such as methanol, ethanol; dimethyl formamide; dimethyl sulfoxide; or halogen containing hydrocarbons, such as chloroform, dichloroethane, chlorobenzene can be used.

The reaction is performed at a temperature of 0° to 200° C., preferably at room temperature or at the boiling temperature of the reaction mixture.

The compounds of the formula I obtained can be isolated from the reaction mixture by methods known per se. In many cases the compound of the formula I or a salt or hydrate thereof precipitates from the reaction mixture and can be eliminated by filtration or centrifuging. If the product does not precipitate from the reaction mixture, it can be precipitated with another solvent, for example water, methanol, or can be isolated by distilling off the organic solvent. The compounds of the formula I obtained, if desired, can be purified by recrystallization, chromatography or boiling with a suitable solvent.

Compounds of the general formula I having a different group from hydrogen in place of R and/or $R^1$ contain a center of asymmetry. The optically active antipodes of the compounds of the formula I can be prepared by starting from optically active compounds of the formula II.

Starting compounds of the formula II, wherein R, $R^1$, $R^2$, $R^3$ and X are as hereinbefore defined can be prepared from compounds of the formula

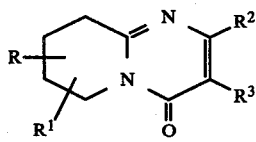

IV wherein R, $R^1$, $R^2$, and $R^3$ are as hereinbefore defined, by halogenation (Arzneimittel Forschung 22 (1972) 815 ). As a halogenating agent elemental halogen, such as bromine; an acid halide, such as sulfuryl chloride; organic halogen derivatives, such as N-bromo-succinimide can be used. The reaction is conducted in an organic solvent, preferably at room temperature, optionally in the presence of an acid binding agent, for example sodium acetate.

The allergic reactions induced by the antigen-antibody interaction may occur in the different tissues and organs accompanied by different symptoms. The most frequent form of the allergy is asthma. As an antiasthmatic agent disodium chromoglycate [1,3-bis-(2-carboxychromon-6-yl-ox)-2-hydroxypropane, Intal$^R$] is widely used, but is not effective orally and it produces the desired effect only by using an inhaler, which makes administration rather complicated. We have now found that the new compounds of the formula I cure the allergic symptoms both orally and intravenously as well as by inhaling.

The efficiency of the compounds of the formula I was proved by standard tests to determine antiallergic activity. The test is carried out by the PCA test-method (Ovary: J. Immun. 81, 355, 1958) and the Church-test (British J. Pharm. 46, 56–66, 1972; Immunology 29, 527–534, 1975) and as a reference substance disodium chromoglycate is used. The test was carried out on rats. The results obtained in PCA test are summarized in Table I.

TABLE I

| Compound | PCA test $ED_{50}$ $\mu$mole/kg. i.v. |
|---|---|
| 9-(phenylhydrazono)-6-methyl-4-oxo-6,7,8,9-tetrahydro-4H—pyrido[1,2-a]-pyrimidine-3-carboxylic acid | 0.60 |
| (+)-9-(phenylhydrazono)-6-methyl-4-oxo-6,7,8,9-tetrahydro-4H—pyrido-[1,2-a]pyrimidine-3-carboxylic acid | 0.29 |
| 9-(4-ethoxyphenylhydrazono)-6-methyl-4-oxo-6,7,8,9-tetrahydro-4H—pyrido-[1,2-a]pyrimidine-3-carboxylic acid | 0.87 |
| 9-(2-carboxyphenylhydrazono)-6-methyl-4-oxo-6,7,8,9-tetrahydro-4H—pyrido-[1,2-a]pyrimidine-3-carboxylic acid | 0.48 |
| 9-(4-carboxyphenylhydrazono)-6-methyl-4-oxo-6,7,8,9-tetrahydro-4H—pyrido-[1,2-a]pyrimidine-3-carboxylic acid | 7.60 |
| 6-methyl-9-(3-nitrophenylhydrazono)-4-oxo-6,7,8,9-tetrahydro-4H—pyrido-[1,2-a]pyrimidine-3-carboxylic acid | 0.52 |
| 9-(3-chlorophenylhydrazono)-6-methyl-4-oxo-6,7,8,9-tetrahydro-4H—pyrido-[1,2-a]pyrimidine-3-carboxylic acid | 0.61 |
| 9-(4-chlorophenylhydrazono)-6-methyl-4-oxo-6,7,8,9-tetrahydro-4H—pyrido-[1,2-a]pyrimidine-3-carboxylic acid | 0.53 |
| 9-(4-bromophenylhydrazono)-6-methyl-4-oxo-6,7,8,9-tetrahydro-4H—pyrido-[1,2-a]pyrimidine-3-carboxylic acid | 0.82 |
| 9-(3-pyridylhydrazono)-6-methyl-4-oxo-6,7,8,9-tetrahydro-4H—pyrido[1,2-a]-pyrimidine-3-carboxylic acid | 0.54 |
| 6-methyl-9-(3-methylphenylhydrazono)-4-oxo-6,7,8,9-tetrahydro-4H—pyrido-[1,2-a]pyrimidine-3-carboxylic acid | 0.42 |
| Disodium chromoglycate | 1.00 |

The above data show that the representatives of the compounds of the general formula I exhibit oral activity as well, whereas disodium chromoglycate is effective only when administered intravenously. Compounds of the formula I are more active also when administered i.v.

The toxicity of the compounds of the formula I is low, generally $LD_{50}$ 500 mg./kg. p.o. on rats and mice.

The compounds of the formula I, in which (a) $R^3$ is aralkyl or halogen and R, $R^1$, $R^2$, $R^4$ and $R^5$ are as hereinbefore defined, (b) $R^4$ is —$(CH_2)_m$—Het (in which n is the integer 1, 2 and 3 and Het stands for a substituted or unsubstituted hetero heterocyclic group) and R, $R^1$, $R^2$, $R^3$ and $R^5$ are as hereinbefore defined, except that $R^4$ and $R^5$ are not linked; or (c) $R^5$ is $C_{1-6}$alkyl or aryl which can be substituted by one or more substituents, and R, $R^1$, $R^2$, $R^3$ and $R^4$ are as hereinbefore defined, except that $R^4$ and $R^5$ are not linked, are new.

The compounds of the formula I may be employed in the form of pharmaceutical compositions containing the active ingredient in association with inert solid or liquid organic or inorganic carriers. The compositions are prepared by methods known per se.

The compositions may be formulated in a form suitable for oral, parenteral administration or for inspiration, such as tablets, dragees, capsules, lozenges, powder mixtures, aerosol sprays, aqueous suspensions or solutions, injection solutions or syrups. The composition can contain suitable solid diluents or carriers, sterilizing aqueous solvents, non-toxic organic solvents. To the compositions suitable for oral administration the usual flavoring or sweetening agents can be added.

As carriers for the tablets suitable for oral administration preferably lactose, sodium citrate, calcium carbonate and disintegrating substances, such as starch, sodium lauryl sulfate, magnesium stearate are used. The carrier of the capsules preferably is lactose of polyethylene glycol. The aqueous suspensions may contain emulsifying and suspending agents. For dilution of the organic solvent suspensions ethanol, glycerin, chloroform, etc. can be used.

The compositions suitable for parenteral administration and inspiration are solutions or suspensions of the active ingredient in a suitable medium, e.g. peanut sesame oil, polypropylene glycol or water. The injection compositions may be administered intramuscularly, intravenously or subcutaneously. The injection solutions are preferably prepared in an aqueous medium and the pH is adjusted to an appropriate value. The solutions may be prepared if desired, in the form of physiological saline or glucose solutions.

The compositions may be administered also by inhalation when curing asthma, by using the conventional inhalating and nebulizing equipment.

The active ingredient content of the pharmaceutical compositions may vary within a wide range and may be 0.005 to 90%.

The daily effective dose depends on the condition, age and weight of the patient and on type of formulation and activity of the active ingredient. The daily oral dosage level generally lies between 0.05 and 15 g./kg. while the daily dosage level generally is 0.001 to 5 mg./kg. at once or in several portions a day when administered intravenously or by inspiration.

The above data are for orientation only, the exact doses should always be prescribed by the physician. Alterations in both directions are allowed.

Further details of the invention are illustrated by the following Examples which are given for illustration and nor for limitation.

EXAMPLE 1

0.73 g. (0.002 moles) of 9,9-dibromo-6-methyl-4-oxo-6,7,8,9-tetrahydro-4H-pyrido[1,2-a]pyrimidine-3-carboxylic acid are dissolved in 2 ml. of dimethyl sulfoxide. To the solution 0.2 ml. (0.002 moles) of phenyl hydrazine and 0.5 ml. (0.004 moles) of N,N-dimethylaniline are added. Thereafter the reaction mixture is allowed to stand for three days. The precipitated crystals are filtered off and washed with methanol. The product is purified by alkaline/acidic precipitation. 0.4 g. (64.0%) of 9-(phenylhydrazono)-6-methyl-4-oxo-6,7,8,9-tetrahydro-4H-pyrido[1,2-a]pyrimidine-3-carboxylic acid are obtained, melting at 254° to 255° C.

Analysis for $C_{16}H_{16}N_4O_3$: calculated: H 61.53%, H 5.16%, N 17.94%; found: H 61.42%, H 5.07%, N 17.85%.

EXAMPLE 2

Following the procedure described in Example 1 but using triethyl amine instead of N,N-dimethylaniline as an acid binding agent, 9-(phenylhydrazono)-6-methyl-4-oxo-6,7,8,9-tetrahydro-4H-pyrido[1,2-a]pyrimidine-3-carboxylic acid is obtained, melting at 255° to 256° C. Yield: 60.5%. The product does not give any melting point depression when admixed with the product of Example 1.

EXAMPLE 3

4.0 g. (0.01 moles) of 3,9,9-tribromo-6-methyl-6,7,8,9-tetrahydro-4H-pyrido[1,2-a]pyrimidine-4-one are dissolved in 10 ml. of dimethyl sulfoxide. To the solution 2.8 ml. (0.03 moles) of phenylhydrazine are added. The reaction mixture is allowed to stand for three days whereupon 20 ml. of water are added. The solvent is decanted from the precipitated substance and the product is recrystallized from methanol. 1.3 g. (34.7%) of 3-bromo-9-(phenylhydrazono)-6-methyl-6,7,8,9-tetrahydro-4H-pyrido[1,2-a]pyrimidine-4-one are obtained, melting at 190° to 192° C.

Analysis for $C_{15}H_{15}N_4OBr$: calculated: C 51.89%, H 4.35%, N 16.14%, Br 23.01%; found: C 51.77%, H 4.43%, N 16.32%, Br 23.31%.

EXAMPLE 4

2.0 g. (0.005 moles) of 9,9-dibromo-6-methyl-4-oxo-6,7,8,9-tetrahydro-4H-pyrido[1,2-a]pyrimidine-3-carboxylic acid ethyl ester and 0.9 g. (0.005 moles) of piperonylic acid hydrazide are dissolved in 80 ml. of pyridine. The solution is allowed to stand for two days whereupon the solvent is distilled off in vacuo. To the residue 30 ml. of water are added. After a short standing the crystals are filtered off and recrystallized from methanol. 0.5 g. (24.2%) of 6-methyl-9-(3,4-methylenedioxybenzoylhydrazono)-4-oxo-6,7,8,9-tetrahydro-4H-pyrido[1,2-a]pyrimidine-3-carboxylic acid ethyl ester are obtained, melting at 183° to 185° C.

Analysis for $C_{20}H_{20}N_4O_6$: calculated: C 58.25%, H 4.89%, N 13.59%; found: C 57.95%, H 4.81%, N 13.42%.

EXAMPLE 5

Following the procedure described in Example 4 but replacing piperonylic acid hydrazide by benzoid acid hydrazide, 9-(benzoylhydrazono)-6-methyl-4-oxo-6,7,8,9-tetrahydro-4H-pyrido[1,2-a]-pyrimidine-3-carboxylic acid ethyl ester is obtained, melting at 209° to 210° C. Yield: 24.7%.

Analysis for $C_{19}H_{20}N_4O_4$: calculated: C 61.96%, H 5.47%, N 15.20%; found: C 61.81%; H 5.39%, N 15.09%.

EXAMPLE 6

To 80 ml. of methanol 11.0 g. (0.03 moles) of 9,9-dibromo-6-methyl-4-oxo-6,7,8,9-tetrahydro-4H-pyrido[1,2-a]pyrimidine-3-carboxylic acid are added. To the suspension 20 ml. of a 50% by weight hydrazine hydrate solution is added in one portion, under vigorous stirring. The temperature of the reaction mixture increases and finally a solution is obtained. The solution is stirred at room temperature for two to three hours and the precipitated crystals are filtered off. The hydrazinium salts separated by filtration is dissolved in 40 ml. of water and the salt is set free by adding solid potassium hydrogensulfate. The precipitated crystals are filtered off, washed with a small amount of water and dried.

Recrystallization from a 50% (v/v) aqueous ethanol solution yield 4.0 g. (65.4%) of 9-hydrazono-6-methyl- 4-oxo-6,7,8,9-tetrahydro-4H-pyrido[1,2-a]pyrimidine-3-carboxylic acid, melting at 202° to 203° C.

Analysis for $C_{10}H_{12}N_4O_3$: calculated: C 50.84%, H 5.12%, N 23.72%; found: C 50.56%, H 5.03%, N 23.57%.

EXAMPLE 7

Into 140 ml. of methanol 18.3 g. (0.05 moles) of 9,9-dibromo-6-methyl-4-oxo-6,7,8,9-tetrahydro-4H-pyrido[1,2-a]pyrimidine-3-carboxylic acid and 10.5 ml. (0.2 moles) of methyl hydrazine are added. The reaction mixture is stirred and allowed to stand for two days. The solvent is distilled off in vacuo. The residue is dissolved in 50 ml. of water and the pH is adjusted to 3 with a 10% by weight hydrochloric acid solution. The precipitated crystals are filtered off, dried and recrystallized from methanol.

5.6 g. (44.8%) of 6-methyl-9-(methylhydrazono)-4-oxo-6,7,8,9-tetrahydro-4H-pyrido[1,2-a]pyrimidine-3-carboxylic acid are obtained, melting at 219° to 220° C.

Analysis for $C_{11}H_{14}N_4O_3$: calculated: C 52.79%, H 5.64%, N 22.39%; found: C 52.61%, H 5.58%, N 22.23%.

EXAMPLES 8 TO 24

1.83 g. (0.005 moles) of 9,9-dibromo-6-methyl-4-oxo-6,7,8,9-tetrahydro-4H-pyrido[1,2-a]pyrimidine-3-carboxylic acid are dissolved in 5 ml. of dimethyl sulfoxide. To the solution 0.005 moles of the monohydrochloride of the corresponding hydrazine derivative indicated in Table II and 1.3 ml. (0.01 moles) of N,N-dimethylaniline are added. The reaction mixture is allowed to stand at room temperature. The precipitated crystals are filtered off and recrystallized from the solvents given in Table II.

EXAMPLES 25 TO 39

1.83 g. (0.005 moles) of 9,9-dibromo-6-methyl-4-oxo-6,7,8,9-tetrahydro-4H-pyrido[1,2-a]pyrimidine-3-carboxylic acid are dissolved in 5 ml. of dimethyl sulfoxide. To the solution 0.015 moles of a hydrazine derivative shown in Table III are added. The reaction mixture is allowed to stand at room temperature for three days. The precipitated crystals are filtered off and recrystallized from the solvents listed in Table III.

TABLE II

| Example No. | Starting hydrazine derivative | Product obtained | Yield (%) | M.p. (°C.) | Solvent for recrystallization | Formula | Analysis (%) calculated / found | | |
|---|---|---|---|---|---|---|---|---|---|
| | | | | | | | C | H | N |
| 8 | 2-bromo-phenyl-hydrazine | 9-(2-bromophenylhydrazono)-6-methyl-4-oxo-6,7,8,9-tetrahydro-4H—pyrido[1,2-a]-pyrimidine-3-carboxylic acid | 47.2 | 265–7 | methanol* | $C_{16}H_{15}N_4O_3Br$ | 49.12 49.09 | 3.86 3.97 | 14.32 14.29 |
| 9 | 3-bromo-phenyl-hydrazine | 9-(3-bromophenylhydrazono)-6-methyl-4-oxo-6,7,8,9-tetrahydro-4H—pyrido[1,2-a]-pyrimidine-3-carboxylic acid | 51.5 | 260–2 | acetic acid | $C_{16}H_{15}N_4O_3Br$ | 49.12 | 3.86 | 14.32 |
| 10 | 4-bromo-phenyl-hydrazine | 9-(4-bromophenylhydrazono)-6-methyl-4-oxo-6,7,8,9-tetrahydro-4H—pyrido[1,2-a]-pyrimidine-3-carboxylic acid | 24.5 | 250–2 | dimethyl-formamide | $C_{16}H_{15}N_4O_3Br$ | 49.12 48.95 | 3.86 3.87 | 14.32 14.34 |
| 11 | 2-chloro-phenyl-hydrazine | 9-(3-chlorophenylhydrazono)-6-methyl-4-oxo-6,7,8,9-tetrahydro-4H—pyrido[1,2-a]-pyrimidine-3-carboxylic acid | 23.1 | 260–2 | dimethyl-formamide | $C_{16}H_{15}N_4O_3Cl$ | 55.42 55.38 | 4.36 4.33 | 16.16 16.25 |
| 12 | 3-chloro-phenyl-hydrazine | 9-(3-chlorophenylhydrazono)-6-methyl-4-oxo-6,7,8,9-tetrahydro-4H—pyrido[1,2-a]-pyrimidine-3-carboxylic acid | 53.4 | 264–5 | acetic | $C_{16}H_{15}N_4O_3Cl$ | 55.42 55.30 | 4.36 4.13 | 16.16 16.07 |
| 13 | 4-chloro-phenyl-hydrazine | 9-(4-chlorophenylhydrazono)-6-methyl-4-oxo-6,7,8,9-tetrahydro-4H—pyrido[1,2-a]-pyrimidine-3-carboxylic acid | 72.0 | 262–4 | dimethyl-formamide | $C_{16}H_{15}N_4O_3Cl$ | 55.42 55.40 | 4.36 4.22 | 16.16 16.07 |
| 14 | 2,4-dichloro-phenyl-hydrazine | 9-(2,4-dichlorophenyl-hydrazono)-6-methyl-4-oxo-6,7,8,9-tetrahydro-4H—pyrido[1,2-a]pyrimidine-3-carboxylic acid | 39.3 | 241–2 | dimethyl- | $C_{16}H_{14}N_4O_3Cl_2$ | 50.41 50.60 | 3.70 3.71 | 14.70 14.83 |
| 15 | 2,6-dichloro-phenyl-hydrazine | 9-(2,6-dichlorophenyl-hydrazono)-6-methyl-4-oxo-6,7,8,9-tetrahydro-4H—pyrido[1,2-a]pyrimidine-3-carboxylic acid | 55.9 | 230–2 | acetic acid | $C_{16}H_{14}N_4O_3Cl_2$ | 50.41 50.59 | 3.70 3.58 | 14.70 14.76 |
| 16 | 3,4-dichloro-phenyl-hydrazine | 9-(3,4-dichlorophenyl-hydrazono)-6-methyl-4-oxo-6,7,8,9-tetrahydro-4H—pyrido[1,2-a]pyrimidine-3-carboxylic acid | 64.1 | 248–9 | acetic acid | $C_{16}H_{14}N_4O_3Cl_2$ | 50.41 50.53 | 3.70 3.69 | 14.70 14.66 |
| 17 | 2-fluoro-phenyl-hydrazine | 9-(2-fluorophenylhydrazono)-6-methyl-4-oxo-6,7,8,9-tetrahydro-4H—pyrido[1,2-a]-pyrimidine-3-carboxylic acid | 47.7 | 225–6 | methanol* | $C_{16}H_{15}N_4O_3F$ | 58.18 58.01 | 4.58 4.50 | 16.96 16.89 |
| 18 | 4-fluoro-phenyl-hydrazine | 9-(4-fluorophenylhydrazono)-6-methyl-4-oxo-6,7,8,9-tetrahydro-4H—pyrido[1,2-a]-pyrimidine-3-carboxylic | 48.8 | 261–2 | methanol* | $C_{16}H_{15}N_4O_3F$ | 58.18 58.32 | 4.58 4.61 | 16.96 16.98 |

TABLE II-continued

| Example No. | Starting hydrazine derivative | Product obtained | Yield (%) | M.p. (°C.) | Solvent for recrystallization | Formula | Analysis (%) calculated / found C | H | N |
|---|---|---|---|---|---|---|---|---|---|
| 19 | 2-methoxyphenylhydrazine | 6-methyl-9-(2-methoxyphenylhydrazono)-4-oxo-6,7,8,9-tetrahydro-4H—pyrido[1,2-a]-pyrimidine-3-carboxylic acid | 48.6 | 215–7 | acetic acid | $C_{17}H_{18}N_4O_4$ | 59.64 / 59.52 | 5.30 / 5.25 | 16.37 / 16.42 |
| 20 | 4-methoxyphenylhydrazine | 6-methyl-9-(4-methoxyphenylhydrazono)-4-oxo-6,7,8,9-tetrahydro-4H—pyrido[1,2-a]-pyrimidine-3-carboxylic acid | 47.0 | 212–4 | nitromethane | $C_{17}H_{18}N_4O_4$ | 59.64 / 59.52 | 5.30 / 5.32 | 16.37 / 16.28 |
| 21 | 2-methylphenylhydrazine | 6-methyl-9-(2-methylphenylhydrazono)-4-oxo-6,7,8,9-tetrahydro-4H—pyrido[1,2-a]-pyrimidine-3-carboxylic acid | 46.0 | 221–2 | dimethylformamide | $C_{17}H_{18}N_4O_3$ | 62.57 / 62.81 | 5.56 / 5.59 | 17.17 / 16.99 |
| 22 | 4-methylphenylhydrazine | 6-methyl-9-(4-methylphenylhydrazono)-4-oxo-6,7,8,9-tetrahydro-4H—pyrido[1,2-a]-pyrimidine-3-carboxylic acid | 62.4 | 242–3 | acetic acid | $C_{17}H_{18}N_4O_3$ | 62.57 / 62.31 | 5.56 / 5.49 | 17.17 / 16.93 |
| 23 | 3-methylphenylhydrazine | 6-methyl-9-(3-methylphenylhydrazono)-4-oxo-6,7,8,9-tetrahydro-4H—pyrido[1,2-a]-pyrimidine-3-carboxylic acid | 47.2 | 242–3 | acetic acid | $C_{17}H_{18}N_4O_3$ | 62.57 / 62.75 | 5.56 / 5.47 | 17.17 / 17.26 |
| 24** | 4-chlorophenylhydrazine | (+)-9-(4-chlorophenylhydrazono)-6-methyl-4-oxo-6,7,8,9-tetrahydro-4H—pyrido[1,2-a]-pyrimidine-3-carboxylic acid $[\alpha]_D^{20} = +190°$ (c = 1, dimethyl-formamide) | 58.0 | 255–6 | dimethylformamide | $C_{16}N_{15}N_4O_3Cl$ | 55.42 / 55.32 | 4.36 / 4.38 | 16.16 / 16.07 |

*boiled
**Instead of (±)-9,9-dibromo-6-methyl-4-oxo-6,7,8,9-tetrahydro-4H—pyrido[1,2-a]pyrimidine-3-carboxylic acid optically active (−)-9,9-dibromo-6-methyl-4-oxo-6,7,8,9-tetrahydro-4H—pyrido[1,2-a]pyrimidine-3-carboxylic acid is used.

TABLE III

| Example No. | Starting hydrazine derivative | Product obtained | Yield (%) | M.p. (°C.) | Solvent for recrystallization | Formula | Analysis (%) calculated / found C | H | N |
|---|---|---|---|---|---|---|---|---|---|
| 25 | phenylhydrazine | (+)-9-(phenylhydrazono)-6-methyl-4-oxo-6,7,8,9-tetrahydro-4H—pyrido[1,2-a]-pyrimidine-3-carboxylic acid | 88.2 | 257–8 | methanol* | $C_{16}H_{16}N_4O_3$ | 61.53 / 61.64 | 5.16 / 5.26 | 17.94 / 18.07 |
| 26** | phenylhydrazine | (+)-9-(phenylhydrazono)-6-methyl-4-oxo-6,7,8,9-tetrahydro-4H—pyrido[1,2-a]-pyrimidine-3-carboxylic acid $[\alpha]_D^{20} = +407°$ (c = 2, dimethylformamide) | 87.7 | 255–6 | methanol* | $C_{16}H_{16}N_4O_3$ | 61.53 / 61.61 | 5.16 / 5.07 | 17.94 / 17.77 |
| 27*** | phenylhydrazine | (−)-9-(phenylhydrazono)-6-methyl-4-oxo-6,7,8,9-tetrahydro-4H—pyrido[1,2-a]-pyrimidine-3-carboxylic acid $[\alpha]_D^{20} = -407°$ (c = 2, dimethylformamide) | 88.0 | 258–9 | methanol* | $C_{16}H_{16}N_4O_3$ | 61.53 / 61.62 | 5.16 / 5.10 | 17.91 / 17.90 |
| 28 | 4-ethoxyphenylhydrazine | (±)-9-(4-ethoxyphenylhydrazono)-6-methyl-4-oxo-6,7,8,9-tetrahydro-4H—pyrido[1,2-a]pyrimidine-3-carboxylic acid | 50.1 | 218–9 | dimethylformamide | $C_{18}H_{20}N_4O_4$ | 60.67 / 60.50 | 5.66 / 5.70 | 15.72 / 15.78 |
| 29** | 4-ethoxyphenylhydrazine | (+)-9-(4-ethoxyphenylhydrazono)-6-methyl-4-oxo-6,7,8,9-tetrahydro-4H—pyrido[1,2-a]pyrimidine-3-carboxylic acid $[\alpha]_D^{20} = +350°$ (c = 0,1, dimethylformamide) | 49.7 | 208–9 | dimethylformamide | $C_{18}H_{20}N_4O_4$ | 60.67 / 60.49 | 5.66 / 5.61 | 15.72 / 15.69 |
| 30 | 2-carboxyphenylhydrazine | (±)-9-(2-carboxyphenylhydrazono)-6-methyl-4-oxo-6,7,8,9-tetrahydro- | 34.4 | 266–7 | dimethylformamide | $C_{17}H_{16}N_4O_5$ | 57.30 / 57.49 | 4.53 / 4.43 | 15.72 / 15.65 |

TABLE III-continued

| Example No. | Starting hydrazine derivative | Product obtained | Yield (%) | M.p. (°C.) | Solvent for recrystallyzation | Formula | Analysis (%) calculated / found C | H | N |
|---|---|---|---|---|---|---|---|---|---|
| 31** | 2-carboxy-phenyl-hydrazine | (+)-9-(2-carboxyphenyl-hydrazono)-6-methyl-4-oxo-6,7,8,9-tetrahydro-4H—pyrido[1,2-a]pyrimidine-3-carboxylic acid $[\alpha]_D^{20} = +222.5°$ (c = 1, dimethylformamide) | 50.2 | 260–2 | dimethyl-formamide | $C_{17}H_{16}N_4O_5$ | 57.30 / 57.52 | 4.53 / 4.49 | 15.72 / 15.62 |
| 32 | 4-carboxy-phenyl-hydrazine | 9-(4-carboxyphenyl-hydrazono)-6-methyl-4-oxo-6,7,8,9-tetrahydro-4H—pyrido[1,2-a]pyrimidine-3-carboxylic acid | 65.5 | 280–1 | methanol* | $C_{17}H_{16}N_4O_5$ | 57.30 / 57.35 | 4.53 / 4.47 | 15.72 / 15.61 |
| 33 | 2-nitro-phenyl-hydrazine | 6-methyl-9-(2-nitrophenyl-hydrazono)-4-oxo-6,7,8,9-tetrahydro-4H—pyrido[1,2-a]-pyrimidine-3-carboxylic acid | 71.1 | 270–2 | methanol* | $C_{16}H_{16}N_5O_5$ | 53.78 / 53.66 | 4.23 / 4.22 | 19.60 / 19.63 |
| 34 | 3-nitro-phenyl-hydrazine | 6-methyl-9-(3-nitrophenyl-hydrazono-4-oxo-6,7,8,9-tetrahydro-4H—pyrido[1,2-a]-pyrimidine-3-carboxylic acid | 58.7 | 263–5 | a 2:1 mixture of dimethyl-formamide and acetic acid | $C_{16}H_{16}N_5O_5$ | 53.78 / 53.57 | 4.23 / 4.19 | 19.60 / 19.71 |
| 35 | 4-nitro-phenyl-hydrazine | 6-methyl-9-(4-nitrophenyl-hydrazono)-4-oxo-6,7,8,9-tetrahydro-4H—pyrido[1,2-a]-pyrimidine-3-carboxylic acid | 51.6 | 256–8 | methanol* | $C_{16}H_{16}N_5O_5$ | 53.78 / 53.47 | 4.23 / 4.11 | 19.60 / 19.58 |
| 36 | 1-naphthyl-hydrazine | 6-methyl-9-(1-naphthyl-hydrazono)-4-oxo-6,7,8,9-tetrahydro-4H—pyrido-[1,2-a]pyrimidine-3-carboxylic acid | 62.3 | 240–1 | acetic acid | $C_{20}H_{18}N_4O_3$ | 66.29 / 65.90 | 5.01 / 5.19 | 15.46 / 15.31 |
| 37 | 2-naphthyl-hydrazine | 6-methyl-9-(2-naphthyl-hydrazono)-4-oxo-6,7,8,9-tetrahydro-4H—pyrido-[1,2-a]pyrimidine-3-carboxylic acid | 46.7 | 172–4 | nitro-methane | $C_{20}H_{18}N_4O_3$ | 66.29 / 66.13 | 5.01 / 4.94 | 15.46 / 15.33 |
| 38 | 3-pyridyl-hydrazine | 6-methyl-9-(3-pyridyl-hydrazono)-4-oxo-6,7,8,9-tetrahydro-4H—pyrido-[1,2-a]pyrimidine-3-carboxylic acid | 51.1 | 236–7 | dimethyl-formamide | $C_{15}H_{15}N_5O_3$ | 57.50 / 57.27 | 4.83 / 4.74 | 22.35 / 22.15 |
| 39*** | 2-carboxy-phenyl-hydrazine | (−)-9-(2-carboxyphenyl-hydrazono)-6-methyl-4-oxo-6,7,8,9-tetrahydro-4H—pyrido[1,2-a]pyrimidine-3-carboxylic acid $[\alpha]_D^{20} = -247.5°$ (c = 1, dimethyl-formamide) | 44.0 | 260–2 | dimethyl-formamide | $C_{17}H_{16}N_4O_5$ | 57.30 / 57.17 | 4.53 / 4.49 | 15.72 / 15.61 |

*Boiled
**Instead of (±)-9,9-dibromo-6-methyl-4-oxo-6,7,8,9-tetrahydro-4H—pyrido[1,2-a]pyrimidine-3-carboxylic acid optically active (−)-9,9-dibromo-6-methyl-4-oxo-6,7,8,9-tetrahydro-4H—pyrido[1,2-a]pyrimidine-3-carboxylic acid is used.
***Instead of racemic (±)-9,9-dibromo-6-methyl-4-oxo-6,7,8,9-tetrahydro-4H—pyrido[1,2-a]-pyrimidine-3-carboxylic acid optically active (+)-9,9-dibromo-6-methyl-4-oxo-6,7,8,9-tetrahydro-4H—pyrido[1,2-a]pyrimidine-3-carboxylic acid is used.

EXAMPLE 40

Following the procedure described in Example 25 but replacing 9,9-dibromo-6-methyl-4-oxo-6,7,8,9-tetrahydro-4H-pyrido[1,2-a]pyrimidine-3-carboxylic acid by 9,9-dibromo-6-methyl-4-oxo-6,7,8,9-tetrahydro-4H-pyrido[1,2-a]pyrimidine-3-carbonitrile and recrystallizing the crude product from acetonitrile 9-(phenylhydrazono)-6-methyl-4-oxo-6,7,8,9-tetrahydro-4H-pyrido[1,2-a]pyrimidine-3-carbonitrile monohydrate is obtained, melting at 222° to 223° C. Yield 41.7%.

Analysis for $C_{16}H_{15}N_5O \cdot H_2O$: calculated: C 61.73%, H 5.50%, N 22.49%; found: C 61.47%, H 5.42%, N 22.67%.

EXAMPLE 41

Following the procedure described in Example 25 but replacing 9,9-dibromo-6-methyl-4-oxo-6,7,8,9-tetrahydro-4H-pyrido[1,2-a]pyrimidine-3-carboxylic acid by 9,9-dibromo-6-methyl-4-oxo-6,7,8,9-tetrahydro-4H-pyrido[1,2-a]pyrimidine-3-carboxamide and recrystallizing the crude product from nitromethane, 9-(phenylhydrazono)-6-methyl-4-oxo-6,7,8,9-tetrahydro-4H-pyrido[1,2-a]pyrimidine-3-carboxamide is obtained, melting at 246° to 247° C. Yield: 40.5%.

Analysis for $C_{16}H_{17}N_5O_2$: calculated: C 61.73%, H 5.50%, N 22.49%; found: C 61.61%, H 5.48%, N 22.40%.

EXAMPLE 42

Following the procedure described in Example 25 but replacing 9,9-dibromo-6-methyl-4-oxo-6,7,8,9-tetrahydro-4H-pyrido[1,2-a]pyrimidine-3-carboxylic acid by 9,9-dibromo-4-oxo-6,7,8,9-tetrahydro-4H-pyrido[1,2-a]pyrimidine-3-carboxylic acid, 9-(phenylhydrazono)-4-oxo-6,7,8,9-tetrahydro-4H-pyrido[1,2-a]pyrimidine-3-carboxylic acid is obtained, melting at 267° to 268° C. Yield: 41.7%.

Analysis for $C_{15}H_{14}N_4O_3$: calculated: C 60.39%, H 4.73%, N 18.78%; found: C 60.18%, H 4.71%, N 18.66%.

EXAMPLE 43

Following the procedure described in Example 25 but replacing 9,9-dibromo-6-methyl-3-oxo-6,7,8,9-tetrahydro-4H-pyrido[1,2-a]pyrimidine-3-carboxylic acid by 9,9-dibromo-7-methyl-4-oxo-6,7,8,9-tetrahydro-4H-pyrido[1,2-a]pyrimidine-3-carboxylic acid, 9-(phenylhydrazono)-7-methyl-4-oxo-6,7,8,9-tetrahydro-4H-pyrido[1,2-a]pyrimidine-3-carboxylic acid is obtained, melting at 260° to 261° C. Yield: 40.1%.

Analysis for $C_{16}H_{16}N_4O_3$: calculated: C 61.52%, H 5.16%, N 17.93%; found: C 61.69%, H 5.07%, N 18.11%.

EXAMPLE 44

Following the procedure described in Example 3 but replacing 3,9,9-tribromo-6-methyl-6,7,8,9-tetrahydro-4H-pyrido[1,2-a]pyrimidine-4-one by 9,9-dibromo-6-methyl-6,7,8,9-tetrahydro-4H-pyrido[1,2-a]pyrimidine-4-one, 9-(phenylhydrazono)-6-methyl-6,7,8,9-tetrahydro-4H-pyrido[1,2-a]pyrimidine-4-one is obtained, melting at 163° to 164° C. Yield: 31.7%.

Analysis for $C_{15}H_{16}N_4O$: calculated: C 67.15%, H 6.01%, N 20.88%; found: C 67.33%, H 6.09%, N 20.77%.

EXAMPLE 45

Following the procedure described in Example 3 but replacing 3,9,9-tribromo-6-methyl-6,7,8,9-tetrahydro-4H-pyrido[1,2-a]pyrimidine-4-one by 9,9-dibromo-3,6-dimethyl-6,7,8,9-tetrahydro-4H-pyrido[1,2-a]pyrimidine-4-one, 9-(phenylhydrazono)-3,6-dimethyl-6,7,8,9-tetrahydro-4H-pyrido[1,2-a]-pyrimidine-4-one is obtained, melting at 165° to 166° C.

Analysis for $C_{16}H_{18}N_4O$: calculated: C 68.06%, H 6.43%, N 19.84%; found: C 67.81%, H 6.59%, N 19.64%.

EXAMPLE 46

1.8 g. (0.005 moles) of 9,9-dibromo-6-methyl-4-oxo-6,7,8,9-tetrahydro-4H-pyrido[1,2-a]-pyrimidine-3-carboxylic acid are dissolved in 5 ml. of dimethyl sulfoxide. To the solution 1.8 g. (0.015 moles) of N-phenyl-N-methyl-hydrazine are added. The reaction mixture is allowed to stand for three days, whereupon 10 ml. of water are added. The solvent is decanted from the precipitated substance and the product is crystallized from methanol.

0.8 g. (49.0%) of 9-(N-phenyl-N-methylhydrazono)-6-methyl-4-oxo-6,7,8,9-tetrahydro-4H-pyrido[1,2-a]pyrimidine-3-carboxylic acid are obtained, melting at 196° to 198° C.

Analysis for $C_{17}H_{18}N_4O_3$: calculated: C 62.57%, H 5.56%, N 17.17%; found: C 62.86%, H 5.36%, N 17.33%.

EXAMPLE 47

Following the procedure described in Example 3 but replacing 3,9,9-tribromo-6-methyl-6,7,8,9-tetrahydro-4H-pyrido[1,2-a]pyrimidine-4-one by 9,9-dibromo-3-ethyl-2,6-dimethyl-6,7,8,9-tetrahydro-4H-pyrido[1,2-a]pyrimidine-4-one, 3-ethyl-9-(phenylhydrazono)-2,6-dimethyl-6,7,8,9-tetrahydro-4H-pyrido[1,2-a]pyrimidine-4-one is obtained, melting at 135° to 137° C. Yield 40.1%.

Analysis for $C_{18}H_{22}N_4O$: calculated: C 69.65%, H 7.14%, N 18.05%; found: C 69.42%, H 7.09%, N 18.00%.

EXAMPLE 48

Following the procedure described in Example 3 but replacing 3,9,9-tribromo-6-methyl-6,7,8,9-tetrahydro-4H-pyrido[1,2-a]pyrimidine-4-one by 9,9-dibromo-3-phenyl-6-methyl-6,7,8,9-tetrahydro-4H-pyrido[1,2-a]pyrimidine-4-one, 3-phenyl-9-(phenylhydrazono)-6-methyl-6,7,8,9-tetrahydro-4H-pyrido[1,2-a]pyrimidine-4-one are obtained, melting at 146° to 148° C. Yield: 45.5%.

Analysis for $C_{21}H_{20}N_4O$: calculated: C 73.23%, H 5.85%, N 16.27%; found: C 73.00%, H 5.81%, N 16.22%.

We claim:

1. A process for the preparation of a nitrogen bridgehead compound of the formula (I)

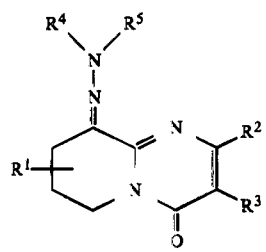

wherein $R^1$ is hydrogen, lower alkyl, styryl, or lower alkoxycarbonyl;

$R^2$ is hydrogen or lower alkyl;

$R^3$ is carboxy, lower alkoxycarbonyl, carbamoyl, cyano, formyl, or lower alkyl;

$R^4$ is hydrogen, lower alkyl, hydroxyethyl, carboxy-lower alkyl, phenyl, naphthyl, phenyl or naphthyl substituted by at least one hydroxy, halogen, lower alkyl, sulfo, carboxy, lower alkoxy, methylenedioxy, amino, nitro or trifluoromethoxy, methoxycarbonyl ethoxycarbonyl, trifluoromethyl, benzyl, 2-, 3- or 4-pyridyl, or benzothiazol-2-yl;

$R^5$ is hydrogen, lower alkanoyl, benzoyl or nicotinoyl or the group $-NR^4R^5$ is piperidinyl, pyrrolidinyl or morpholinyl, or a pharmaceutically acceptable salt, hydrate, stereoisomer, optically active isomer, geometric isomer or tautomer thereof, which comprises reacting a racemic or optically active compound of the formula (II)

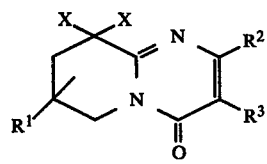
wherein X is halogen, with a compound of the formula
(III)
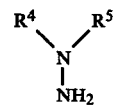
or a pharmaceutically acceptable acid addition salt thereof, at a temperature of 0° to 200° C.
2. The process defined in claim 1 wherein the reaction takes place under vigorous stirring for a period of 2 to 3 hours.
3. The process defined in claim 1 wherein the reaction takes place over a period of 2 to 3 days, standing.
* * * * *